United States Patent [19]

Haynes et al.

[11] Patent Number: 4,980,297
[45] Date of Patent: Dec. 25, 1990

[54] DEVICE FOR THE MEMBRANE SEPARATION OF THE COMPONENTS OF A LIQUID SAMPLE

[75] Inventors: John L. Haynes, Chapel Hill, N.C.; Nicholas A. Grippi, Nutley, N.J.

[73] Assignee: Becton, Dickinson and Company, Franklin Lakes, N.J.

[21] Appl. No.: 19,829

[22] Filed: Feb. 27, 1987

[51] Int. Cl.$^5$ .............................................. G01N 1/18
[52] U.S. Cl. ...................................... 436/178; 436/63; 422/44; 422/101; 422/104; 210/247; 210/321.6; 210/433.1; 210/649; 128/760; 128/762; 128/764; 604/414
[58] Field of Search ............... 422/101, 104, 44–48; 210/247, 321.6, 433.1, 649, 927; 128/760, 762, 763, 764; 604/414; 436/63, 177, 178

[56] References Cited

U.S. PATENT DOCUMENTS 3,604,410 9/1971 Whitacre .............................. 128/762
4,564,359 1/1986 Rühland ............................ 422/44 X
4,639,316 1/1987 Eldegheidy .................. 210/433.2 X

FOREIGN PATENT DOCUMENTS 0184852 6/1986 European Pat. Off. .............. 422/44

Primary Examiner—Robert J. Warden
Assistant Examiner—Lynn M. Kummert
Attorney, Agent, or Firm—John L. Voellmicke

[57] ABSTRACT

A device for the separation of a separable component from a liquid sample for use with an evacuated receptable includes a housing having an interior cavity and a separator membrane dividing the cavity into a first portion and a second portion. The separator membrane has a porosity selected for the desired separation thereacros. An inlet structure is provided for fluid communication between the first portion of the interior cavity and the source of the liquid sample. Communication structure is provided for allowing fluid communication between one of the portions of the cavity and the evacuated receptacle. A rigid receptacle is in fluid communication with the other of the portions of the cavity.

31 Claims, 10 Drawing Sheets

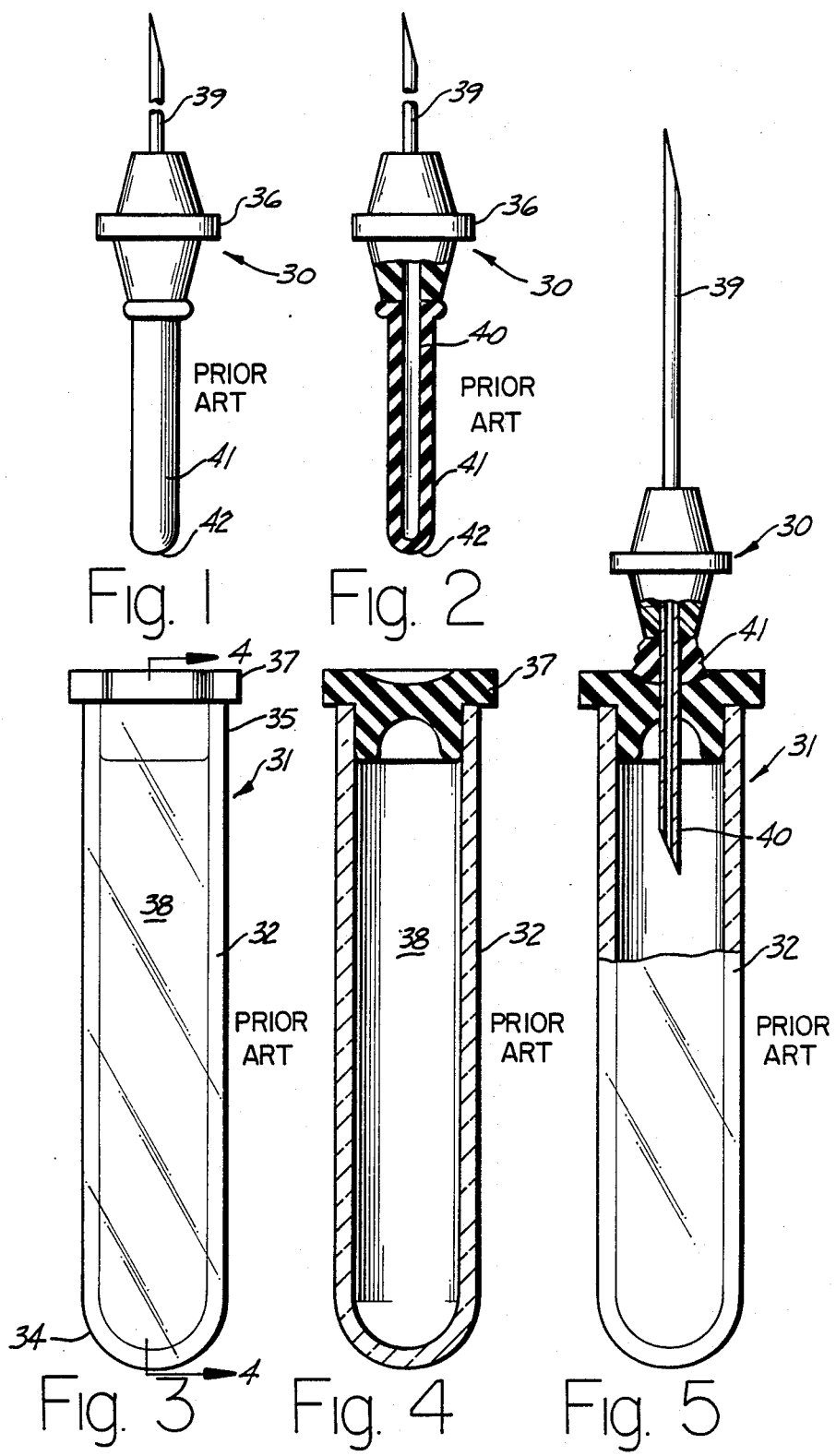

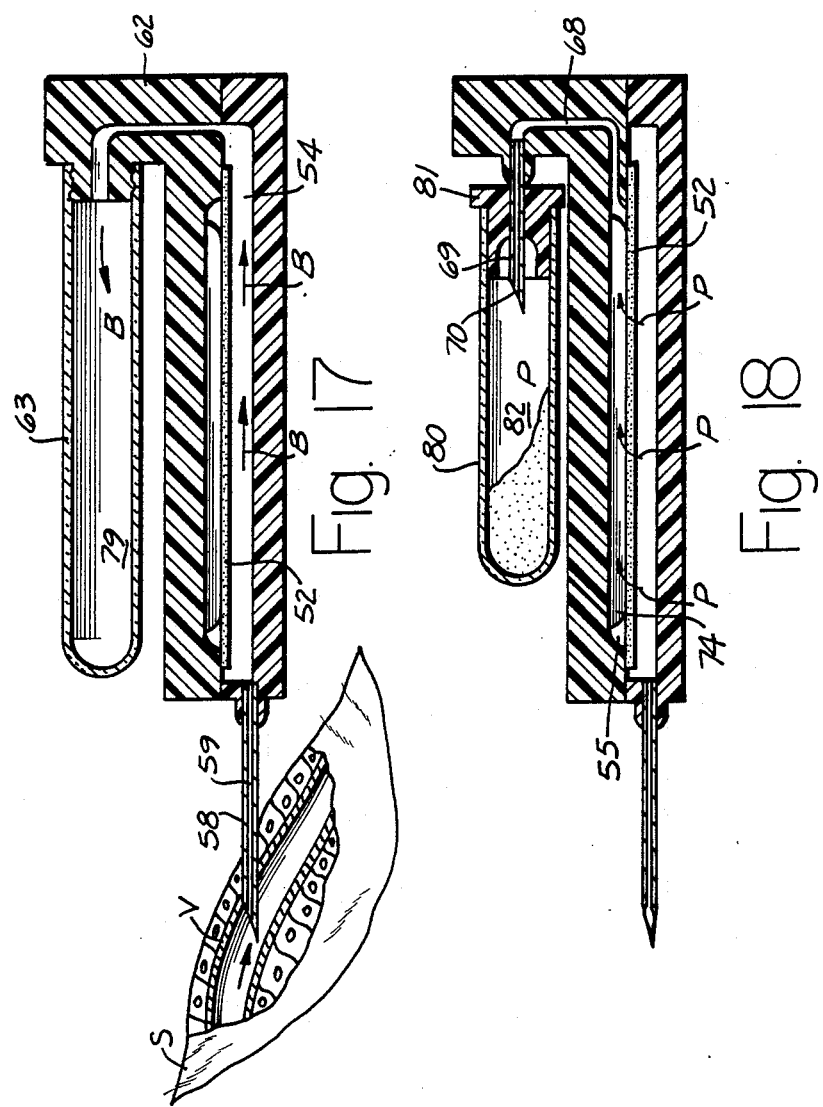

DEVICE FOR THE MEMBRANE SEPARATION OF THE COMPONENTS OF A LIQUID SAMPLE

BACKGROUND OF THE INVENTION

1. Field of the Invention

The present invention relates to devices for membrane separation of a separable component from a liquid sample. More particularly, this invention relates to self-contained devices for separation of the liquid component from the cellular component of a blood sample without the use of a centrifuge, an auxiliary circulating system, an auxiliary pump or the like and a method for using these devices.

2. Description of the Prior Art

A common method of obtaining a blood sample involves the use of a two-cannula needle assembly and an evacuated glass tube having a pierceable stopper. The method involves inserting one cannula of the needle assembly into the subject's vein and piercing the stopper of the evacuated glass tube with the other cannula of the needle assembly, thereby establishing fluid communication between the vein and the interior of the glass tube. Due to the lower pressures within the evacuated glass tube blood is drawn from the subject into the tube. Evacuated tubes and needle assemblies for use therewith are described in U.S. Pat. No. 3,469,572 to Nehring. Such devices are commercially available under the VACUTAINER Brand name from Becton, Dickinson and Company, Franklin Lakes, N.J.

The blood sample, in the evacuated glass tube, may then be placed in a centrifuge and centrifuged until the more dense cellular component of the blood sample is driven to the bottom of the tube and the less dense plasma is positioned at the top of the sample. The stopper from the tube may then be removed and the plasma sample poured off for subsequent testing. If serum is desired the blood sample is allowed to clot before centrifuging the blood sample.

U.S. Pat. No. 4,057,499 to Buono teaches the collection of a plasma or serum sample using a sampling member having a hollow interior for the collection of liquid and a piston connected to one end of the sampling member. The piston includes a lip for forming a seal with the interior walls of the sample containing glass tube and an interior portion contains a filter and a one-way valve. In use, a blood sample, in a glass tube, is centrifuged to separate the liquid and the cellular phases and then the device of Buono is placed in the tube and forced along the inner tube surface so that the piston passes through the liquid portion of the sample forcing the liquid portion through the filter and through the valve into the hollow interior of the device. The device containing a portion of the liquid sample is then removed from the glass tube. Buono teaches that it is desirable to physically separate the liquid phase of the sample from the cellular phase to prevent deleterious chemical interaction between the two. Accordingly, Buono teaches the use of a centrifuge and a separate filtering apparatus to obtain the plasma or serum sample.

It is known that forcing a blood sample through a filter membrane is not a practical method of separating the liquid and the cellular components because the filter membrane would soon become caked with the cellular components and unable to perform its task as a filter. Accordingly, it is believed that if the liquid phase of the blood sample is to be filtered from the cellular portion of the blood sample, without the use of a centrifuge, a cross-flow filter arrangement should be provided. In a cross-flow arrangement, the blood sample flows across the surface of the filter membrane in a direction parallel to the major axis of the membrane while a secondary force provides a pressure differential between the blood side of the membrane and the liquid side so that the liquid phase will pass through the membrane. U.S. Pat. Nos. 3,211,645; 4,191,182; 4,212,742 and 4,343,705 teach various devices for the filtration of liquid using a cross-flow technique. In each of these patents, the devices utilized require an applied pressure driving force from a separate source across the membrane filter in order to bring about the proper separation. That is, a separate pumping and/or circulating device must be used in conjunction with the cross-flow filter.

It is believed that the cross-flow method of filtration is superior because when the blood sample is caused to flow in parallel relationship across the filter membrane there is less tendency for the membrane to be clogged by the cellular portion of the blood sample and therefore allowing the blood to be filtered without the use of a centrifuge. In any event, all of the devices and methods described hereinabove require the use of relatively expensive support devices such as a centrifuge, liquid pumping and/or circulating systems, or the like. In addition, dependency on additional equipment can consume valuable time in emergency situations wherein the liquid phase of the patient's blood sample must be analyzed properly in order to diagnose the problem and/or to provide proper emergency treatment. In these situations, it is desirable to provide a device for the separation of the liquid phase of the blood sample from the cellular phase immediately upon the drawing of the blood sample without further steps.

U.S. Pat. No. 3,705,100 to Blatt et al. teaches a device for separating plasma from whole blood, without the use of a centrifuge or recirculating pumps, which involves drawing a blood sample from the patient, apparently using a hypodermic syringe. After the blood is drawn, the needle or other apparatus is removed from the syringe and the syringe is connected to a filter housing and spring means which provides positive pressure to the contents of the syringe through the syringe plunger. Blood is driven through the syringe tip around a circular pathway and out into the environment where it is collected in an open container while plasma passes through the filter medium and drips into a second reservoir. While the teachings of Blatt et al. provide for plasma separation without the use of a centrifuge or separate pumping and/or circulating devices it still has deficiencies in that it requires multiple handling steps with respect to the blood sample exposing the person taking the sample with potential for being contaminated by the blood sample. In addition, the sample can be exposed to the environment during the procedure using the Blatt et al. device thereby possibly compromising any laboratory results at any laboratory analysis of the plasma obtained therefrom.

Incorporated by reference is the patent application of Oberhardt et al. presently assigned to the assignee hereof (Ser. No. 694,717 and filed on Jan. 25, 1985) which teaches an improved device for the separation of the lighter fraction from the heavier fraction of a liquid sample which operates without the use of additional equipment such as centrifuges and pumps to produce an isolated quantity of the lighter fraction of the liquid. The device of Oberhardt et al. avoids the multiple steps and exposure to the environment of the device taught by Blatt et al. Oberhardt et al. teach a device for separating plasma from blood separating the lighter fraction from the heavier fraction of a liquid sample for use with two evacuated receptacles having a housing with an interior cavity and a membrane separator dividing the interior cavity into a first portion and a second portion. Inlet means is provided for fluid communication between the first portion of the cavity and the source of the liquid sample and first communication means is provided for communication between the first portion of the cavity and an evacuated receptacle. A second communication means is provided for fluid communication between the second portion of the interior cavity and a second evacuated receptacle. When used with blood, the device of Oberhardt et al. can be connected directly to the patient wherein the first and second evacuated tubes are placed in fluid communication with the first and second communication means so that the blood flow sample flows through the inlet means along the separator membrane through the first communication means and into the first evacuated receptacle, simultaneously, plasma is drawn through the membrane and the second communication means and into the second evacuated receptacle. The device of Oberhardt et al. overcomes the deficiency of the prior art devices while allowing a blood sample to be taken directly from the patient and into evacuated receptacles without being exposed to the environment. Oberhardt et al. also teach a method using the device described hereinabove comprising the steps of withdrawing blood from the patient across the surface of the separator membrane and simultaneously drawing plasma from the blood through the membrane while the blood is being withdrawn from the patient.

The device of Oberhardt et al. is a substantial improvement over the prior art blood separation devices. However, it requires the use of two evacuated receptacles and depending on the porosity of the separation membrane and the structure of the communication means for connecting the interior of the housing with the evacuated receptacle it may be necessary to coordinate the fluid communication between the two receptacles so that they are connected, for example, simultaneously to avoid vacuum loss through the unconnected fluid communication means in the housing.

The prior art teaches devices and methods for separating the liquid phase from the cellular phase of a blood sample while it is being drawn from the patient using two separate evacuated receptacles. There is still a need for a simple, straight-forward, reliable, easily fabricated device for the membrane separation of the components of a liquid sample, for example, separating a non-particulate phase from a particulate phase of a liquid, or separating plasma from blood as it is being withdrawn from the patient wherein the system will operate with a single evacuated receptacle to reduce the complexity of the system and to eliminate the need for specialty apparatus or procedural complexity involved with timing of the activation of multiple evacuated tubes with the device.

SUMMARY OF THE INVENTION

An operable device for the separation of a separable component from a liquid sample for use with a rigid evacuated receptacle includes a housing having an interior cavity and a separator membrane dividing the cavity into a first portion and a second portion. The separator membrane has a porosity selected for the desired separation thereacross. Also included is inlet means for providing fluid communication between the first portion of the cavity and the source of the liquid sample and communication means for providing fluid communication between one of the portions of the cavity and the evacuated receptacle. A rigid receptacle is in fluid communication with the other of the portions of the cavity.

In accordance with another embodiment of the present invention an operable device for the separation of plasma from a blood sample for use with a rigid evacuated receptacle having an open end and a pierceable stopper or barrier sealing the open end includes a housing having an interior cavity and a separator membrane dividing the cavity into a first blood receiving portion and a second plasma receiving portion. The separator membrane has a pore size within the range of between about 0.2 micron and 1.5 microns. Also included is inlet means for providing fluid communication between the blood receiving portion and the source of the blood sample and communication means for providing fluid communication between one of the portions of the cavity in the evacuated receptacle. A rigid receptacle is in fluid communication with the other of the portions of the cavity. The communication means and the rigid receptacle are positioned so that when the inlet means is in fluid communication with the source of the blood sample and the communication means is in fluid communication with the evacuated receptacle the evacuated receptacle causes the partial evacuation of the cavity and the partial evacuation of the rigid receptacle causing the blood sample to flow through the inlet means along the membrane and into one of the receptacles, simultaneously, plasma is drawn through the membrane and the second plasma receiving portion into the other of the receptacles.

Another aspect of the present invention includes a method of separating a separable component from a liquid sample using a device including a housing having an interior cavity and a separator membrane dividing the cavity into a first portion and a second portion. The separator membrane has a porosity selected for the desired separation thereacross. Also included is inlet means for providing fluid communication between the first portion and the source of the liquid sample and communication means for providing fluid communication between one of the portions of the cavity and the evacuated receptacle. A rigid receptacle is in fluid communication with the other portions of the cavity. The method includes establishing fluid communication between the inlet means and the source of the liquid sample and establishing fluid communication between an evacuated receptacle and the communication means so that the evacuated receptacle causes the partial evacuation of the cavity and the rigid receptacle, causing the liquid sample to flow through the inlet means along the membrane and into one of the receptacles, simultaneously, the separable component of the liquid sample is drawn through the membrane and the second portion into the other of the receptacles.

Another embodiment of the instant invention is a method for separating plasma from blood comprising; withdrawing the blood from a patient across the surface of a separator membrane having a porosity selected for separating plasma from blood; and simultaneously drawing plasma from the blood through the membrane into an evacuated receptacle while the blood is being withdrawn from the patient.

In accordance with the principles of the present invention, a number of advantages are achieved. Primarily, the present invention provides a simple, straightforward, reliable, easily fabricated device for membrane separation of a separable component from a liquid sample, for example, separating a non-particulate component from a particulate component of a liquid sample or separating plasma from blood as it is being withdrawn from the patient wherein the system will operate with a single evacuated receptacle to reduce the complexity of the system and to eliminate any specialty apparatus such as pumps and centrifuges or to eliminate procedural complexity involved with timing of the activation of multiple evacuated tubes with the device.

BRIEF DESCRIPTION OF THE DRAWINGS

FIG. 1 is a side elevation view representing a known blood collection needle assembly;

FIG. 2 is a partial cross-sectional view of the needle assembly of FIG. 1 illustrating the second cannula and the internal structure of the resilient sleeve;

FIG. 3 is a side elevation view of a known evacuated blood collection tube;

FIG. 4 is a cross-sectional view of the evacuated tube of FIG. 3 taken along line 4—4;

FIG. 5 is a partial cross-sectional view illustrating the interaction between the needle assembly of FIG. 1 and the evacuated tube of FIG. 3 when the second cannula of the needle assembly pierces the stopper of the evacuated tube;

FIG. 17 is a partial cross-sectional view of the device of FIG. 15 taken substantially along line 17—17;

FIG. 18 is a cross-sectional view of the device of FIG. 15 taken along line 18—18;

DETAILED DESCRIPTION

Figure 6:
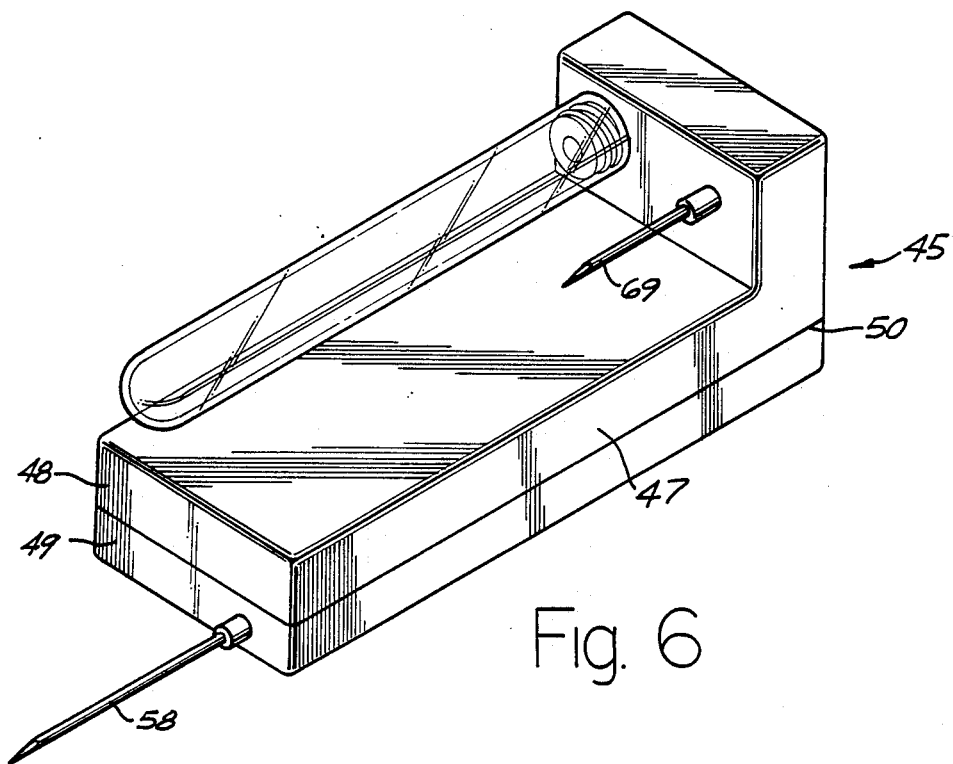
FIG. 6 is a perspective view of a preferred embodiment of the device for separation of plasma from a blood sample of the present invention.
Figure 7:
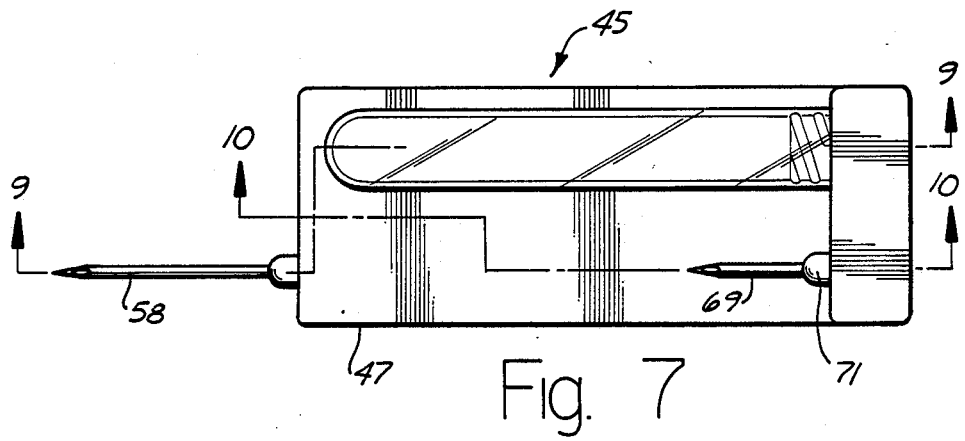
FIG. 7 is a top plan view of the device of FIG. 6.
Figure 8:
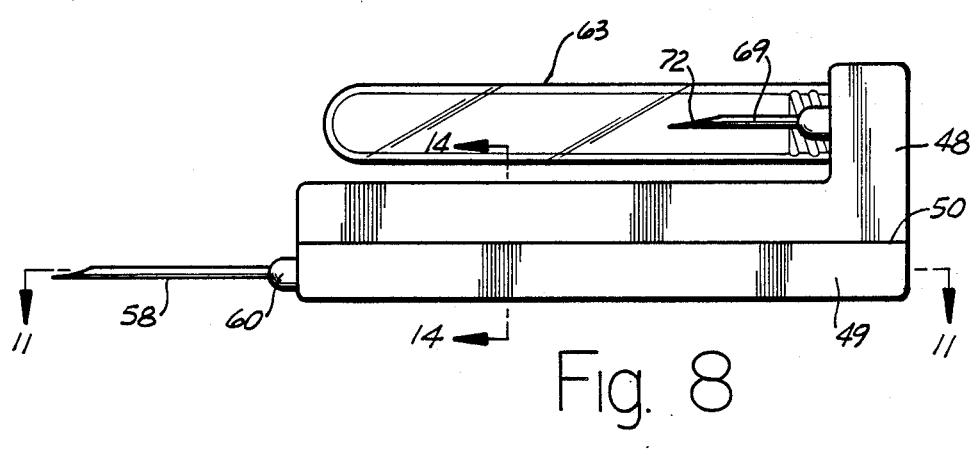
FIG. 8 is a side elevation view of the device of FIG. 6.
Figure 9:
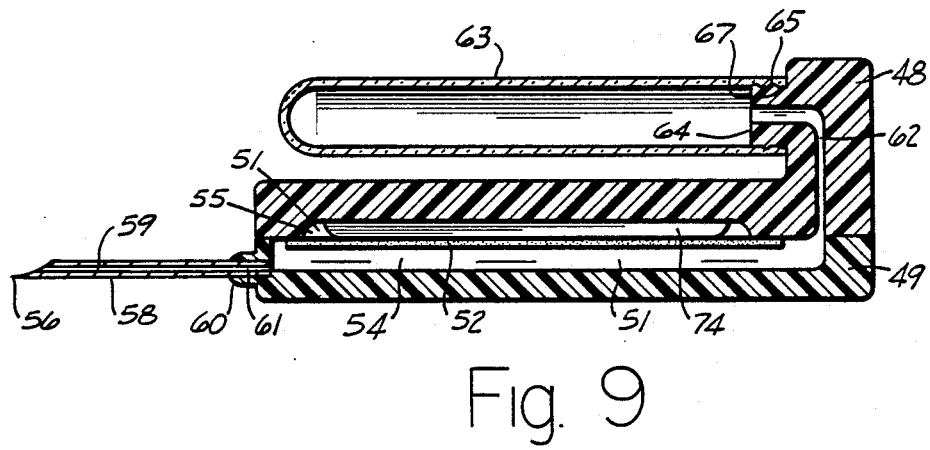
FIG. 9 is a cross-sectional view of the device of FIG. 7 taken along line 9—9.
Figure 10:
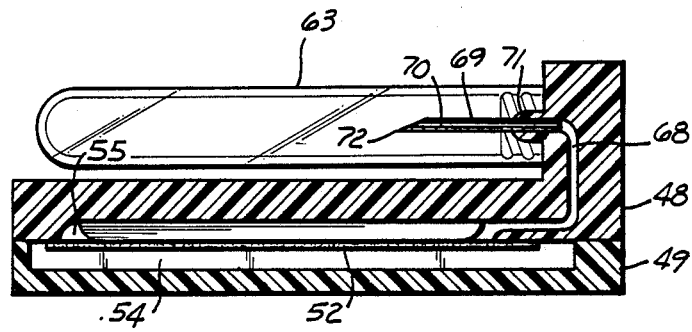
FIG. 10 is a cross-sectional view of the device of FIG. 7 taken along line 10—10.
Figure 11:
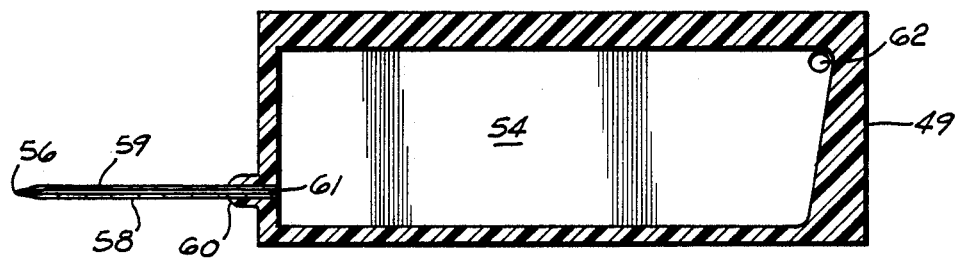
FIG. 11 is a cross-sectional view of the device of FIG. 8 taken along line 11—11.
Figure 12:
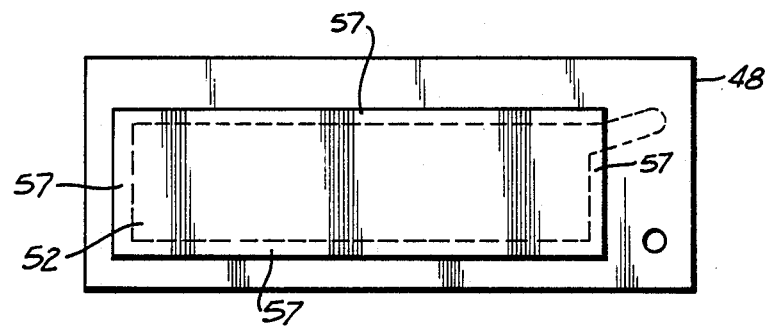
FIG. 12 is a bottom plan view of the upper housing portion of the device of FIG. 6 illustrating the separator membrane attached to the upper housing portion.
Figure 13:
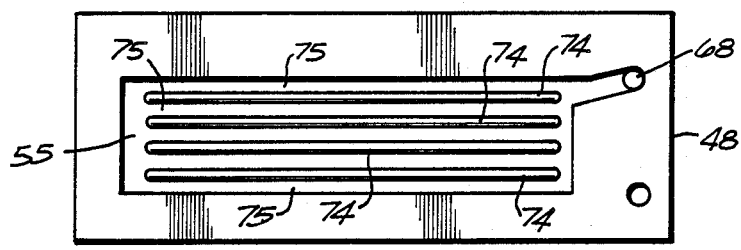
FIG. 13 is a bottom plan view of the upper housing portion of the device of FIG. 6 similar to the view of FIG. 12, but without the separator membrane.
Figure 14:
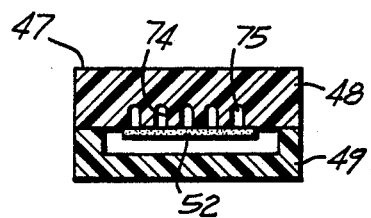
FIG. 14 is a cross-sectional view of the device of FIG. 8 taken along line 14—14.
Figure 15:
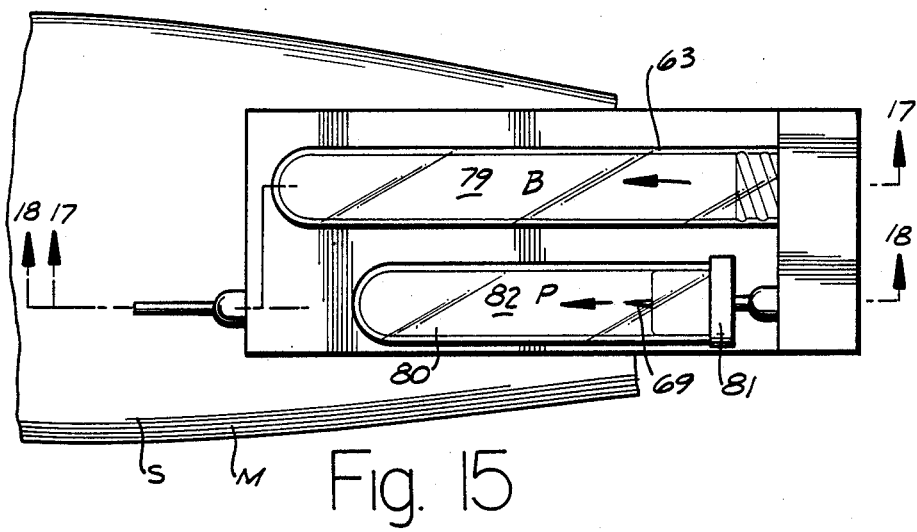
FIG. 15 is a top plan view of the device of FIG. 6 in use with an evacuated tube, taking a blood sample.
Figure 16:
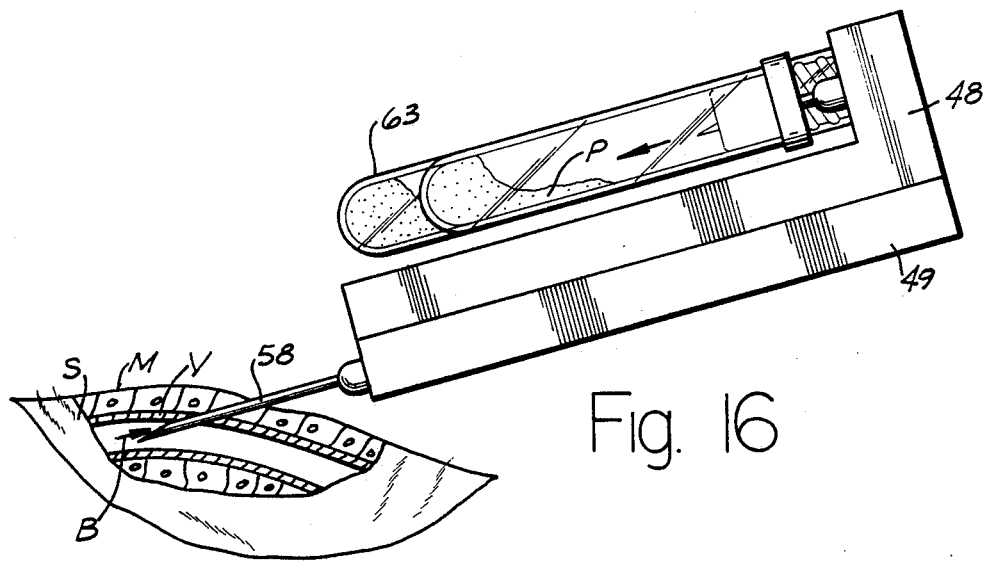
FIG. 16 is a side elevation view of the device of FIG. 15, in use taking a blood sample.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-5, known prior art blood collection devices include a blood collection needle 30 and a blood collection evacuated glass tube 31. The blood collection tube includes a cylindrical glass body 32 with closed end 34 and neck portion 35. The neck portion is sealed by a resilient pierceable stopper 37 which is applied to the tube while both components are in a reduced pressure environment so that the interior portion 38 has an absolute internal pressure which is less than atmospheric pressure.

The blood collection needle includes a hub 36, a first cannula 39 adapted to pierce a patient's flesh and enter a blood containing vein therein. Second cannula 40 is adapted to pierce stopper 37 to establish fluid communication between the patient's vein and the interior of the evacuated glass tube so that a blood sample is drawn from the patient into the tube. The first cannula and second cannula of the blood collection needle may be separate cannulae in fluid communication with each other through the hub or they may be part of one cannula which passes through the hub. Some blood collection needles include a resilient sleeve which prevents blood from leaving the blood collection needle after venipuncture. A resilient sleeve 41 includes a closed end 42 which is adapted to be pierced by second cannula 40 upon the application of external force to the sleeve in the direction along the longitudinal axis of cannula 40. This force can be applied by forcing the blood collection tube stopper onto the second cannula, as best illustrated in FIG. 5. After the blood sample is taken, the evacuated tube is removed from the blood collection needle and the resilient sleeve returns to its original position which allows it to prevent further blood from leaving the blood collection needle. It can be seen that this type of needle assembly will allow several tube samples to be taken from the same venipuncture because the second cannula is sealed after each tube is removed therefrom. Blood collection needle hubs commonly have external threads (not shown) to interact with a tube holder (not shown) to facilitate guiding the tube toward the second cannula so that the cannula pierces the central, thinner, portion of the stopper.

The blood sample, in the evacuated tube, may be placed in a centrifuge (not shown) and spun until the more dense cellular component of the blood sample is driven to the closed end portion of the tube and the less dense plasma is positioned above the cellular component closer to the neck portion. The stopper from the tube may then be removed and the plasma poured off for subsequent testing. Also, serum may be obtained by allowing the blood sample to coagulate before centrifuging the blood sample. The serum or plasma produced is used in various types of blood testing equipment which analyze the contents thereof to provide data with respect to the state of the patient's blood.

Referring now to FIGS. 6–14, a preferred device 45 for separation of plasma from a blood sample for use with an evacuated receptacle, such as the blood collection evacuated glass tubes hereinabove described, includes housing 47 comprising upper housing portion 48 and lower housing portion 49 joined along line 50 to form an interior cavity 51.

A separator membrane 52 divides interior cavity 51 into a first blood receiving portion 54 and a second plasma receiving portion 55. Separator membrane 52 is attached to upper housing portion 48 along sealing area 57 of the upper housing portion, via heat sealing, ultrasonic welding, solvent adhesive or other suitable means, so that fluid passing from blood receiving portion 54 to plasma receiving portion 55 must pass through membrane separator 52. It will be apparent to one skilled in the art that there are numerous constructions which will allow the separation of housing portions by a membrane, for example, clamping the membrane between the housing portions, and that the structure recited hereinabove is exemplary of these many possibilities.

An injection cannula 58 having a lumen 59 therethrough is attached to a hollow hub portion 60 of the lower housing portion via adhesive or other suitable means. Lower housing portion 49 also includes an inlet conduit 61 providing fluid communication between lumen 59 and blood receiving portion 54. The injection cannula includes a sharpened distal tip 56 adapted to pierce the subject's flesh and enter a vein therein to provide the blood sample. It is within the purview of the present invention to include a structure wherein the injection cannula is separated from the housing portion by a length of flexible tubing so that the housing portion need not be positioned at the injection site but may be conveniently placed closely thereto. A blood communication conduit 62 communicates between blood receiving portion 54 and upper housing portion 48. The blood communication conduit is opposed from inlet conduit 61 so that blood passing from the inlet conduit to the blood communication conduit travels in a direction along the length of separator membrane 52 to establish a cross-flow relationship between the blood and the membrane. A rigid receptacle 63 is connected to the upper housing portion at threaded boss 64 via internal threads 67 formed in the receptacle engaging external threads 65 on the boss. It will be apparent to one skilled in the art that numerous methods may be used to join the rigid receptacle to the upper housing portion. Such methods include adhesive bonding, ultrasonic welding, an interference fit between the inside diameter of the receptacle and the outside diameter of the boss and that the threaded engagement between the rigid receptacle and the upper housing portion is merely exemplary of these many possibilities. It is also within the purview of the present invention to include a rigid receptacle that is integrally formed with the housing and rigid receptacles that are permanently attached or removably connected to the housing.

A needle cannula 69 having a lumen 70 therethrough is attached to a hub portion 71 of the upper housing portion via adhesive or other suitable means. The needle cannula includes a sharpened tip 72 adapted to pierce the stopper or barrier of an evacuated blood collection tube. The upper housing portion also includes a plasma communication conduit 68 which allows fluid communication between the lumen of the needle cannula and plasma receiving portion 55 of the housing.

In order to support separator membrane 52 when vacuum forces are applied, as will be explained in more detail hereinafter, support ribs 74 are provided in plasma receiving portion 55 of the upper housing. In the preferred embodiment these ribs are arranged in a parallel arrangement with recesses 75 adjacent to the support ribs for allowing the flow of plasma from the membrane to plasma communication conduit 68. In the preferred embodiment the ribs are formed integrally with the upper housing portion. It is within the purview of the present invention to include other structures to support the membrane against the vacuum forces. These other structures include, but are not limited to: a separate panel, having raised surfaces, inserted in the upper housing portion; a structural screen supporting the membrane; and structural material laminated to the membrane and heat sealed to the housing portion.

FIGS. 15–18 depict the preferred device for the separation of plasma from a blood sample in use. Initially, injection cannula 58 is inserted through the skin S of a mammalian body M so that lumen 59 thereof is in fluid communication with the blood B in vein V. Immediately after the fluid communication with the vein is established, a rigid evacuated collection tube 80 is guided along upper housing portion 48 so that needle cannula 69 pierces a stopper 81 of the evacuated collection tube and there is fluid communication between interior 82 and the lumen of cannula 69. At this point evacuated tube 80 will cause the partial evacuation of the interior cavity of the housing and interior 79 of rigid receptacle 63 so that first blood receiving portion 54, second plasma receiving portion 55 and the receptacles are at a substantially equal subatmospheric pressure as the blood flows through lumen 59 into blood receiving portion 54. Although the preferred embodiment, illustrates the evacuated receptacle in direct fluid communication with second plasma receiving portion 55 of the device which is across separator membrane 52 from blood receiving portion 54, from a filtering standpoint in most applications it may not matter which receptacle is evacuated and applied at the time of sample taking and which receptacle is not evacuated. However, in specific applications, depending on the liquid being filtered and the separator membrane chosen, it may be relevant as to which side of the separator membrane is in fluid communication with the evacuated receptacle. Accordingly, it is within the purview of the present invention to include embodiments wherein the evacuated receptacle will be in direct fluid communication with the blood receiving portion of the housing while the rigid receptacle will be in direct fluid communication with the plasma receiving portion of the housing. It is also within the purview of the present invention to include embodiments wherein the rigid receptacle is removable and the evacuated receptacle is not removable, and embodiments where both the rigid receptacle and the evacuated receptacle are removable. It is desirable to have the removable receptacle in direct fluid communication with the plasma receiving portion of the housing because after the sample is separated it is more convenient to simply withdraw the removable receptacle from the cannula and conveniently deliver it to the laboratory for analysis.

With the evacuated tube connected to the device, as best illustrated in FIGS. 17 and 18, rigid receptacle 63, now partially evacuated by action of evacuated tube 80, creates a vacuum force within the housing through membrane 52 which draws blood from vein V through lumen 59 of cannula 58, through blood receiving portion 54 along the surface of membrane 52 and, finally, through blood communicating conduit 62 into interior 79 of blood collecting rigid receptacle 63. At the same time that rigid receptacle 63 is drawing blood through the device, evacuated collection tube 80 is providing a vacuum force on the side of membrane 52 opposite from the blood supply. The vacuum force created by collection tube 80 causes plasma from the stream of blood flowing through blood receiving portion 54 to cross through separator membrane 52 into plasma receiving portion 55 of the housing. The plasma is guided along the housing by support ribs 74, through plasma communication conduit 68 and the lumen of needle cannula 69 into interior 82 of evacuated collection tube 80.

It is believed that the vacuum forces on both sides of the separator membrane are approximately equal before blood enters the blood receiving portion of the housing. When blood fills the blood receiving portion of the housing it lowers the vacuum forces on that side of the separator membrane so that there are greater vacuum forces in the plasma receiving portion of the housing than in the blood receiving portion. This resulting vacuum force differential is believed to be the force which drives the plasma through the separator membrane.

When the pressure inside rigid receptacle 63 and evacuated collection tube 80 is approximately equal to the blood pressure of the subject, evacuated collection tube 80 will contain a quantity of plasma, separated from the blood, ready for use. Further, receptacle 63 will contain a quantity of blood, still containing plasma, which may be held aside pending the outcome of the analysis of the plasma from tube 80. An advantage of the present invention is that it produces samples in two separate tubes. Accordingly, each tube can be sent to a different physical area for storage and/or testing as opposed to separation processes where the plasma and the remaining portion of the blood are contained in the same tube.

Separator membrane 52 is constructed so that it contains pores having a diameter selected so that plasma from a blood sample can flow through the membrane while the cellular components of the blood sample are too large to pass therethrough. It is desirable to use a membrane having a pore size within the range of between about 0.2 micron and 1.5 microns. It is preferred that the membrane has a pore size within the range of between about 0.4 micron and 0.6 micron.

If additional plasma or serum is required, depending on the time element, rigid receptacle 63 may be removed from the device and spun, in a centrifuge, to provide this additional fluid. Accordingly, a rigid receptacle containing anticoagulant may be used so that the blood sample does not clot and plasma may still be obtained.

In the preferred device injection cannula 58, and needle cannula 69 can be chosen from the range of sizes of commercially available blood collection needles. It is preferred that injection cannula 58 be within the range of about 20 gauge to 22 gauge and have a length within the range of about one inch to 1.5 inches (25 mm to 38 mm). The needle cannula is preferably within the range of about 20 gauge to 22 gauge and having a length of about 0.635 inches (16 mm).

A wide range of separator membrane sizes can be used with the present invention, depending on the variables associated with the various other elements. With respect to plasma separation, a separator membrane having an area within the range of about 11 $cm^2$ to 32 $cm^2$ is desirable when using commercially available evacuated tubes. In the preferred embodiment the separator membrane is sized so that approximately 11 $cm^2$ of area is available for transfer of plasma from the blood receiving portion 54 to plasma receiving portion 55. Also, it is believed that it is generally desirable to have the ratio of length to width of the separator membrane to be in the range of about 4/1 to 10/1 when separating plasma from blood. It should be noted that the volume of the empty space within the interior cavity of the housing, the inlet conduit, the blood communication conduit and the plasma communication conduit should be held to the lowest possible practical value to minimize the amount of air that will be drawn into the evacuated collection tube in order to fill this empty space with blood or plasma. This air, when it enters the evacuated collection tube reduces the amount of vacuum force available for drawing and separating the blood sample.

For separating plasma from blood a vacuum of about 0.33 atmosphere is believed to be desirable. This vacuum may be achieved by constructing the housing so that the empty space within the device, except for the rigid receptacle, is approximately the same volume as the interior volume of the rigid receptacle, and by using the resulting device with an evacuated receptacle being evacuated to about one (1) atmosphere and having an interior volume of about the same as the rigid receptacle Although the preferred embodiment is described using a membrane suitable for separating plasma from whole blood, it is within the purview of the instant invention to include embodiments suitable for the membrane separation of a separable component from a liquid sample, for example, the separation of a non-particulate phase from a particulate phase of a liquid sample, or the separation of a lighter fraction of a liquid from a heavier fraction of a liquid sample, or the separation of any components of a liquid sample for which a separator membrane can discriminate such as separating a liquid portion from a colloidal suspension or separating small molecular species from a blood sample. Accordingly, membranes such as known ultrafiltration membranes and known non-woven membranes having suitable pore ratings may be used as components of the instant invention for separating the light and heavy components of a liquid sample.

Figure 19:
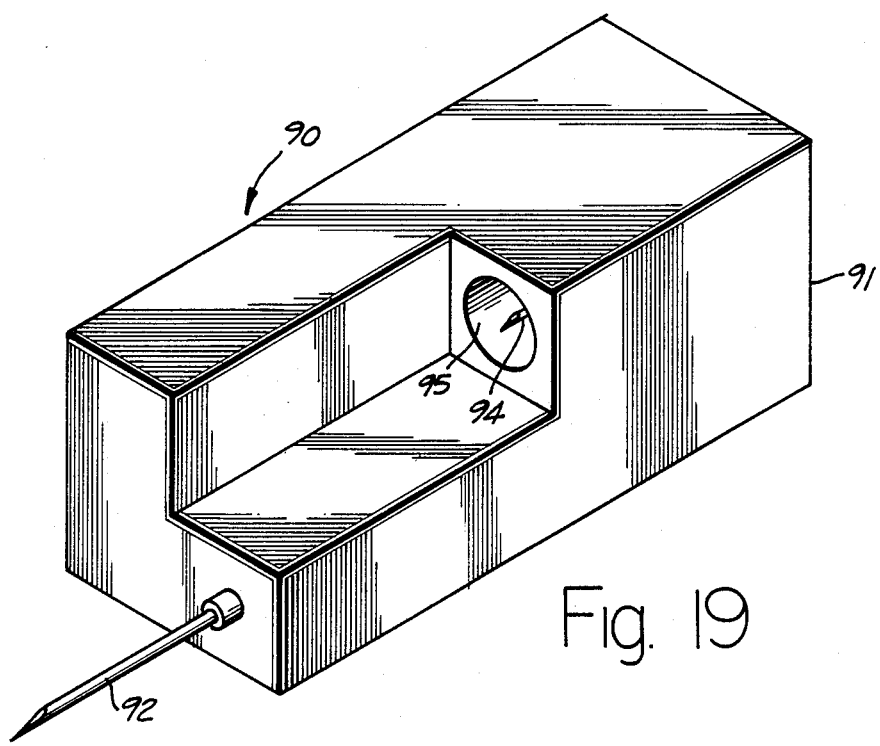
FIG. 19 is a perspective view of an alternative embodiment of the preferred device for separation of plasma from a blood sample.
Figure 20:
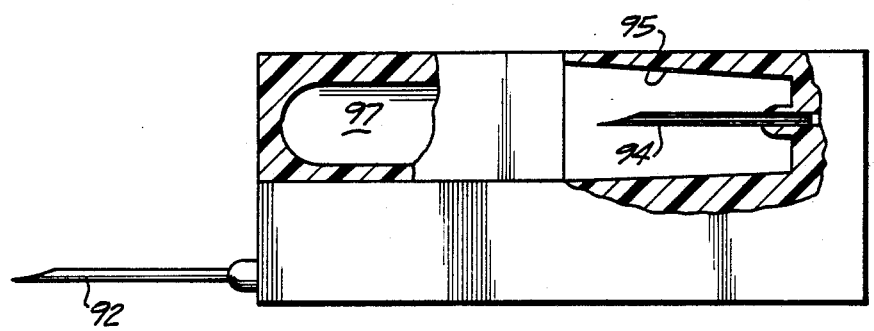
FIG. 20 is a side elevation view of the device of FIG. 19 partially cross-sectioned to illustrate the structure surrounding the needle cannula and the rigid receptacle.

Referring now to FIGS. 19 and 20, an alternative embodiment 90 of the present device functions in substantially the same manner as the above-described preferred embodiment. This embodiment includes housing 91 having injection cannula 92 and needle cannula 94. This embodiment differs from previously described embodiments in that housing 91 includes a frusto-conically shaped recess 95 concentrically positioned around the needle cannula. The purpose of recess 95 is to provide a surface to guide the pierceable stopper (not shown) of the evacuated glass tube (not shown) into engagement with the needle cannula so that the needle cannula pierces the central, thinner, portion of the pierceable stopper. With the frusto-conically shaped recess functioning as a guide means for the evacuated tubes, the operator can more easily engage the evacuated tube with the device.

Further, in embodiment 90 the rigid blood receiving receptacle is integrally formed with housing 91 within the area indicated as 97. In this embodiment, after the evacuated tube draws in the plasma sample it is removed from the device. Device 90 is then discarded or destroyed in a safe manner to eliminate potential contamination of medical personnel handling the remainder of the blood sample. This feature is especially desirable when dealing with patients having diseases such as AIDS wherein the patient's blood is potentially dangerous to other persons. In this situation, the instant invention provides a convenient device for separating the blood and discarding the unused portion in one safe step without intervening handling steps.

Figure 21:
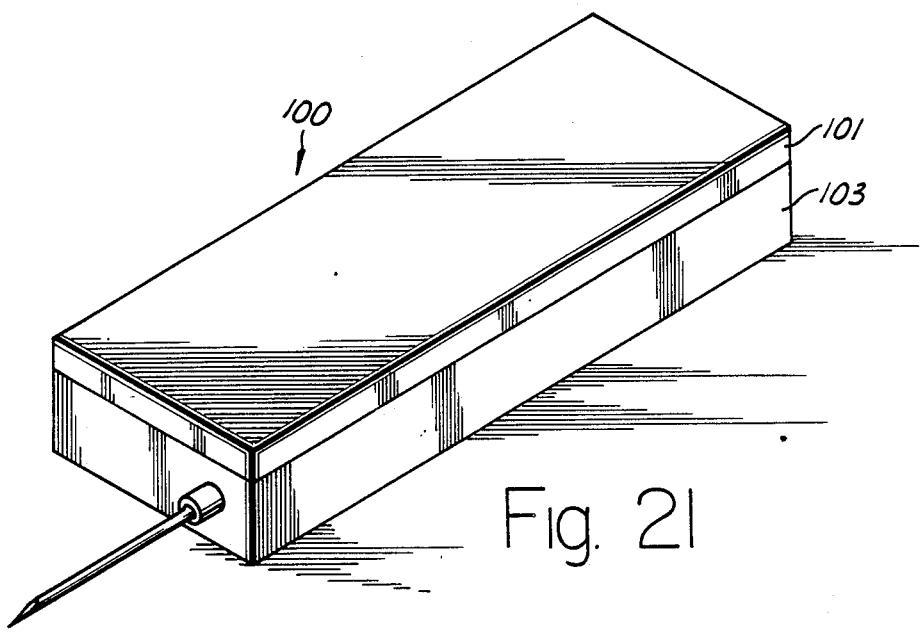
FIG. 21 is a perspective view of another alternative embodiment of the preferred device for the separation of plasma from a blood sample.
Figure 22:
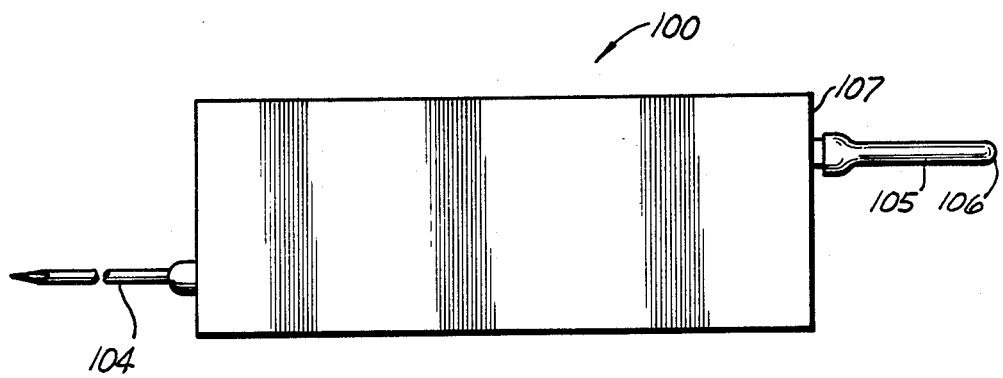
FIG. 22 is a top plan view of the device of FIG. 21.

Adverting to FIGS. 21 and 22, another alternative embodiment of the present invention 100 includes upper housing portion 101, and lower housing portion 103 having injection cannula 104 protruding from the distal end thereof. A needle cannula (not shown) protrudes from the proximal end of upper housing portion 101 and is covered by a resilient sleeve 105. Sleeve 105 includes closed end 106 which is adapted to be pierced by the injection cannula upon the application of external force applied to the resilient sleeve in a direction along the cannula toward upright wall 107 of upper housing portion 101 to allow fluid passage through a needle cannula. Sleeve 105 will return to its original position upon termination of the external force. This embodiment functions in substantially the same manner as above-described embodiments. This embodiment differs from the previously described embodiments in that the needle cannula projects in a direction opposite of injection cannula 104. Also, the rigid receptacle (not shown) is integrally formed in lower housing portion 103 rather than in the upper portion as with the embodiment of FIGS. 19 and 20. The plasma separated from the blood will be drawn into the needle cannula and into the evacuated receptacle (not shown). When the evacuated receptacle is removed from the needle cannula, resilient sleeve 105 will return to its original position thus sealing the needle cannula to the environment, another useful feature of this embodiment. This embodiment illustrates that there are many possible combinations for positioning the injection cannula and the needle cannula and for integrating the rigid receptacle into the structure of the device and that the embodiments described herein represent only a few of the many possibilities.

Figure 23:
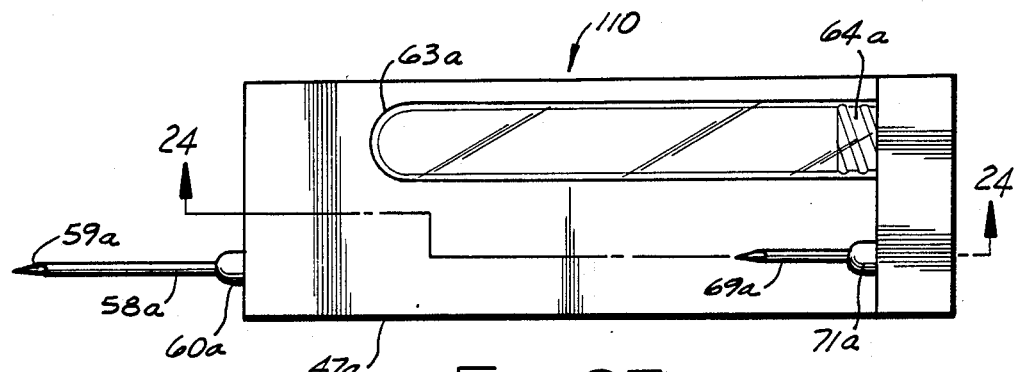
FIG. 23 is a top plan view of still another alternative embodiment of a preferred device for separation of plasma from a blood sample.
Figure 24:
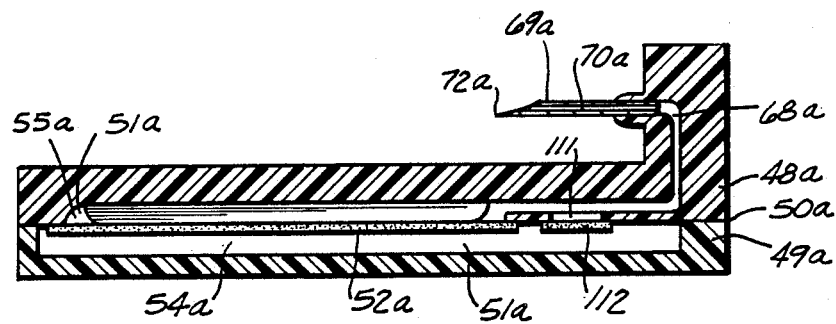
FIG. 24 is a cross-sectional view of the device of FIG. 23 taken along line 24—24.

FIGS. 23 and 24 illustrate another alternative embodiment of the present invention. This alternative embodiment functions in a similar manner to the embodiment of FIGS. 1 through 14 and includes many components which are substantially identical to the components of the embodiment of FIGS. 6–14. Accordingly, similar components performing similar functions will be numbered identically to those components in the embodiment of FIGS. 6–14, except that a suffix "a" will be used to identify these components in FIGS. 23 and 24. An alternative embodiment 110 of the device for the separation of plasma from a blood sample for use with an evacuated receptacle includes a housing 47 *a* comprising an upper housing portion 48a and a lower housing portion 49a joined along line 50a to form an interior cavity 51a.

A separator membrane 52a divides interior cavity 51a into a first blood receiving portion 54a and a second plasma receiving portion 55a. Membrane separator 52a is attached to upper housing portion 48a via heat sealing, ultrasonic welding, adhesive or other suitable means, so that liquid passing from blood receiving portion 54a to plasma receiving portion 55a must pass through membrane separator 52a.

An injection cannula 58a having a lumen 59a therethrough is attached to hollow hub portion 60a of the lower housing portion to provide for fluid communication between the lumen of cannula 59a and blood receiving portion 54a of the housing.

A blood communication conduit (not shown) communicates between the blood receiving portion 54a and upper housing portion 48a. The blood communication conduit is opposed from injection cannula 58a so that blood passing from the injection cannula to the blood communicating conduit travels in a direction along the length of separator membrane 52a to establish a cross-flow relationship between the blood and the membrane. A rigid receptacle 63a is connected to the upper housing portion at boss 64a via adhesive sealing the boss to the inside diameter of the open end of the rigid receptacle. It is also within the purview of the instant invention to include a rigid receptacle which includes a rubber plug at the distal end which engages a cannula attached to the upper housing portion and in fluid communication with the blood receiving portion.

A needle cannula 69a having a lumen 70a therethrough is attached to a hub portion 71a of the upper housing portion via adhesive or other suitable means. The needle cannula includes a sharpened tip 72a adapted to pierce the stopper or barrier of an evacuated blood collection tube. The upper housing portion also includes a plasma communication conduit 68a which allows fluid communication between the lumen of the needle cannula and the plasma receiving portion 55a of the housing.

Upper housing portion 48a also includes aperture 111 which is covered by an air-permeable liquid-impermeable element 112 so that all gases passing through aperture 111 must pass through element 112. The air-permeable, liquid-impermeable element is porous and capable of developing sufficiently high surface tension under liquid contact to serve as a barrier against liquid passage therethrough during normal use of the instant device.

Air-permeable, liquid-impermeable element 112 is preferably a thin porous membrane having a maximum pore rating of generally between about 0.01 micron to 0.5 micron and desirably about 0.5 micron. The air-permeable, liquid-impermeable element may also, take the form of a plug which occludes aperture 111 or a plug having an aperture which is in turn occluded or covered by an air-permeable, liquid-impermeable element. It will be apparent to one skilled in the art that numerous constructions can be used to cover an aperture in a housing with an air-permeable, liquid-impermeable element and that the structures described hereinabove are exemplary of these many possibilities. Also, it is within the purview of the present invention to include structure wherein the entire plug for sealing aperture 111 is made of air-permeable, liquid-impermeable material.

In use, the injection cannula 58a may be inserted through the skin of the patient so that lumen 59a is in fluid communication with a vein. Immediately after fluid communication with a vein is established, a rigid evacuated tube (not shown) is guided over needle cannula 69a so that needle cannula 69a pierces the stopper or barrier of the evacuated tube and there is fluid communication between the interior of the evacuated tube and plasma communication conduit 68a. At this point the evacuated tube will cause the partial evacuation of interior cavity 51 of the housing and rigid receptacle 63a. To increase the speed at which rigid receptacle 63a is evacuated the added area of aperture 111 is provided. The presence of aperture 111 reduces the amount of time necessary for the blood receiving portion, the plasma receiving portion and the rigid receptacle to become partially evacuated to a subatmospheric pressure which approximates that in the evacuated tube. Aperture 111 is covered or occluded by an air-permeable, liquid-impermeable membrane so that as blood flows through the blood receiving portion of the housing it will contact element 112 to seal aperture 111 and preventing liquid passage therethrough.

The housing of the present invention may be constructed of a wide variety of materials such as metals, plastics and ceramics. Plastic materials are more desirable because of their ability to be molded into a wide variety of complex shapes and for compatibility with blood. Transparent thermoplastic materials are preferred so that the operability of the device can be observed through the housing walls. A wide variety of metals and plastics are suitable for the various cannulae of the present invention, with medical grade stainless steel being preferred. The choice of material for the separator membrane will depend on the composition of the materials being separated and the sizes of the particles which should be effectively blocked from passing through the membrane. Commercially available dialyzing membranes and ultrafiltration membranes may be used. Representative of such membranes are polycarbonate and polyester membranes having a pore size of within the range of between about 0.2 micron and 1.5 microns as manufactured by Nucleopore Corporation of Pleasanton, Calif., U.S.A.

The resilient sleeve is preferably made of self-sealing elastomeric materials such as rubber and thermoplastic elastomers.

Air-permeable, liquid-impermeable materials in thin sheet or membrane form, or in more substantial thicknesses which can be formed into plugs, are known and available for use in element 112. For example, W. L. Gore and Associates, Inc. of Elkton, Md. produces filter material known as GORE-TEX membranes which are capable of being air-permeable, liquid-impermeable elements. Air-permeable, liquid-impermeable membranes are available in polymeric materials such as polytetrafluoroethylene, polyester, polyvinylchloride, polypropylene, polyethylene and the like desirably ranging in thickness from about 0.003 to 0.010 inches (0.0076 to 0.0025 cm). It is also possible to laminate the air-permeable, liquid-impermeable membrane material to a backing sheet which will provide increased structural integrity and stability to the structure to help prevent the air-permeable, liquid-impermeable element from being damaged during use. Some nonwoven fabrics are suitable for this backing sheet in as much as they are porous and can be relatively thin while being strong. In this respect, although other materials may be chosen, such non-woven materials may be selected from the group of materials consisting of polypropylene, polyethylene and polyester. It is possible to choose a backing sheet material which has good heat sealing properties so that, with a plastic housing, the element may be sealed over aperture 111 in the housing. In this case, the air-permeable, liquid-impermeable element may be chosen primarily for its performance characteristics and the backing sheet can be chosen for its processability characteristics to improve the overall structure of the assembled product. Also, the element or the element laminated to a backing sheet, may be heat sealed or attached to a plug or cap having a conduit therethrough. The plug or cap can then be forced into or over aperture 111 or in some way attached to the aperture in the housing during the assembly process. This form of manufacture may be desirable because in cases where the element is not properly attached only the plug will have to be discarded rather than an entire housing portion.

Thus the present invention provides a simple, straightforward, reliable, easily fabricated device for the membrane separation of a separable component from a liquid sample, for example, separating a first non-particulate phase from a second particulate phase of a liquid sample, or separating a lighter fraction from the heavier fraction of a liquid sample, or separating plasma from blood as it is being withdrawn from the patient wherein the system will operate with a single evacuated receptacle to reduce the complexity of the system and to eliminate any specialty apparatus or problems involved with timing of the activation of the evacuated tubes with the device. The instant invention may be used to produce an isolated quantity of the lighter fraction of a liquid sample, for example, an isolated quantity of plasma being collected in the blood is being withdrawn from the patient.

What is claimed is:

1. A method of separating a separable component from a liquid sample using a device including a housing having an interior cavity, a separator membrane dividing said cavity into a first portion and a second portion, said separator membrane having a porosity selected for desired separation thereacross, inlet means for providing fluid communication between said first portion and a source of a liquid sample, a rigid receptacle in fluid communication with one of said portions of said cavity, and communication means for providing fluid communication between the other of said portions of said cavity and an evacuated receptacle comprising:
   establishing fluid communication between said inlet means and the source of the liquid sample; and
   establishing fluid communication between an evacuated receptacle and said communication means so that said evacuated receptacle causes partial evacuation of said cavity and said receptacle, causing the liquid sample to flow through said inlet means along said membrane and into one of said receptacles, simultaneously, the separable component of the liquid sample being drawn through said membrane and said second portion into the other of said receptacles.

2. A method of separating plasma from a blood sample using a device including a housing having an interior cavity, a separator membrane dividing said cavity into a first blood receiving portion and a second plasma receiving portion, said separator membrane having a porosity selected for separating plasma from blood, inlet means for providing fluid communication between said blood receiving portion and a source of the blood sample, a receptacle in fluid communication with one of said portions of said cavity, and communication means for providing fluid communication between the other of said portions of said cavity and an evacuated receptacle comprising:
  establishing fluid communication between said inlet means and the source of the blood sample; and
  establishing fluid communication between an evacuated receptacle and said communication means so that said evacuated receptacle causes the partial evacuation of said cavity and said receptacle causing the blood sample to flow through said inlet means along said membrane and into one of said receptacles, simultaneously, plasma being drawn though said membrane and said plasma receiving portion, into the other of said receptacles.

3. The method of claim 2 wherein the step establishing fluid communication between said inlet means and the source of the blood sample includes inserting a needle cannula into a patient's body so that blood is drawn directly from the body of the patient into said inlet means.

4. A method of separating plasma from a blood sample using an evacuated receptacle comprising:
  withdrawing blood from a patient;
  directing said blood, as it is being withdrawn from a patient, along a surface of a separator membrane having a porosity selected for separating plasma from blood; and
  simultaneously, causing plasma from said blood to be drawn through said membrane and the into said evacuated receptacle.

5. A method of separating plasma from blood comprising:
  withdrawing blood from a patient across a surface of a separator membrane, having a porosity selected for separating plasma from blood; and
  simultaneously drawing plasma from said blood through said membrane and then into an evacuated receptacle while said blood is being withdrawn from the patient.

6. An operable device for the separation of a separable component from a liquid sample for use with a rigid evacuated receptacle having an open end and a pierceable barrier sealably closing the open end comprising:
  a housing having an interior cavity;
  a separator membrane dividing said cavity into a first portion and a second portion, said separator membrane having a porosity selected for a desired separation thereacross;
  inlet means for providing fluid communication between said first portion and a source of the liquid sample;
  communication means for providing fluid communication between one of said portions of said cavity and an evacuated receptacle; and
  a rigid receptacle in fluid communication with the other of said portions of said cavity, said communication means and said rigid receptacle being positioned so that when said inlet means is in fluid communication with the source of the liquid sample and said communication means is in fluid communication with the evacuated receptacle, the evacuated receptacle causes partial evacuation of said cavity and said rigid receptacle, causing the liquid sample to flow through said inlet means along said membrane and into one of said receptacles, simultaneously, the separable component of the liquid being drawn through said membrane and said second portion into the other of said receptacles.

7. The device of claim 6 wherein said rigid receptacle is removably attached to said housing.

8. The device of claim 6 wherein said communication means is in fluid communication with said second portion of said housing.

9. The device of claim 6 wherein said rigid receptacle is integrally formed with said housing.

10. The device of claim 6 further including air-permeable, liquid-impermeable means positioned to allow gas to pass between said first portion and said second portion while preventing liquid from passing therethrough.

11. The device of claim 10 wherein said air-permeable, liquid-impermeable means includes a filter element being porous and capable of developing sufficiently high surface tension under liquid contact to serve as a barrier against liquid passage therethrough during normal use of said device.

12. The device of claim 11 wherein said filter element is a filter membrane having a maximum pore rating of about 0.5 micron.

13. The device of claim 12 wherein said filter element is made of material selected from the group consisting of polytetrafluoroethylene, polyester, polyvinylchloride, polypropylene and polyethylene.

14. The device of 11 wherein said filter element is a plug having a maximum pore rating of 0.5 micron.

15. The device of claim 6 wherein said communication means includes a needle cannula having a lumen therethrough for piercing the pierceable barrier of the evacuated receptacle to establish fluid communication therewith.

16. The device of claim 15 wherein said needle cannula is covered by a resilient sleeve to prevent fluid passage therethrough, said sleeve including a closed end adapted to be pierced by said cannula upon the application of external force to said sleeve in a direction along said cannula thus allowing fluid passage through said cannula, said sleeve further adapted to return to its original position upon termination of the external force.

17. The device of claim 6 further including support means for supporting said separator membrane against vacuum forces in said second portion.

18. The device of claim 6 wherein said separator membrane has a pore size within the range of between about 0.2 micron and 1.5 microns.

19. The device of claim 6 wherein said separator membrane has a pore size within the range of between about 0.4 micron 0.6 micron.

20. The device of claim 6 wherein said separator membrane is made of material selected from the group consisting of polycarbonate and polyester.

21. The device of claim 6 wherein said inlet means includes an inlet needle cannula having a lumen therethrough and a sharp distal end adapted to pierce the source of the liquid sample to establish fluid communication therewith.

22. An operable device for the separation of plasma from a blood sample for use with a rigid evacuated receptacle having an open end and a pierceable barrier sealing the open end comprising:
  a housing having an interior cavity;
  a separator membrane dividing said cavity into a first blood receiving portion and a second plasma receiving portion, said separator membrane having a pore size of within the range of between about 0.2 micron and 1.5 microns;

inlet means for providing fluid communication between said blood receiving portion and a source of the blood sample;

communication means for providing fluid communication between one of said portions of said cavity and an evacuated receptacle; and a rigid receptacle in fluid communication with the other of said portions of said cavity, said communication means and said rigid receptacle being positioned so that when said inlet means is in fluid communication with the source of the blood sample and said communication means is in fluid communication with the evacuated receptacle, the evacuated receptacle causes partial evacuation of said cavity and said rigid receptacle, causing the blood sample to flow through said inlet means along said membrane and into one of said receptacles, simultaneously, plasma being drawn through said membrane and said second plasma receiving portion into the other of said receptacles.

23. The device of claim 22 wherein said communication means including a needle cannula having a lumen therethrough for piercing a pierceable barrier of an evacuated receptacle to establish fluid communication therewith.

24. The device of claim 23 wherein said needle cannula is covered by a resilient sleeve to prevent fluid passage therethrough, said sleeve including a closed end adapted to be pierced by said cannula upon application of external force to said sleeve in a direction along said cannula thus allowing fluid passage through said cannula, said sleeve further adapted to return to its original position upon termination of the external force.

25. The device of claim 22 wherein said separator membrane has a pore size within the range of between about 0.4 micron and 0.6 micron.

26. The device of claim 22 wherein said inlet means includes an injection cannula having a lumen therethrough and a sharp distal end adapted to be inserted in a patient's vein and establish fluid communication therewith.

27. The device of claim 22 wherein said rigid receptacle is removably attached to said housing.

28. The device of claim 22 wherein said communication means is in fluid communication with said second portion of said housing.

29. The device of claim 22 wherein said rigid receptacle is integrally formed with said housing.

30. The device of claim 22 further including air-permeable, liquid-impermeable means positioned to allow gas to pass between said first portion and said second portion while preventing liquid from passing therethrough.

31. The device of claim 30 wherein said air-permeable, liquid-impermeable means includes a filter element being porous and capable of developing sufficiently high surface tension under liquid contact to serve as a barrier against liquid passage therethrough during normal use of said device.

* * * * *